United States Patent [19]

Pajerski et al.

[11] Patent Number: 4,697,661
[45] Date of Patent: Oct. 6, 1987

[54] DRIVE DESIGN FOR MOBILE X-RAY UNITS WITH DUAL WHEEL DRIVES

[75] Inventors: Michael J. Pajerski, Waukesha; Steven J. Gray, Mukwonago; Gerald K. Flakas, Oconomowoc; Dennis J. Cotic, Waukesha, all of Wis.

[73] Assignee: General Electric Company, Milwaukee, Wis.

[21] Appl. No.: 885,484

[22] Filed: Jul. 14, 1986

[51] Int. Cl.$^4$ .............................. B62D 11/04
[52] U.S. Cl. ...................... 180/6.5; 74/471 R; 180/19.3; 180/332; 180/333
[58] Field of Search ............. 180/6.24, 6.5, 19.1, 180/19.3, 315, 332, 333, 334; 74/470, 471 R, 484, 486, 488, 489

[56] References Cited

U.S. PATENT DOCUMENTS

| 3,340,941 | 9/1967 | Neu | 180/6.5 |
| 3,814,199 | 6/1974 | Jones | 180/6.5 |
| 4,511,825 | 4/1985 | Klimo | 180/6.5 |

Primary Examiner—John J. Love
Assistant Examiner—Donn McGiehan
Attorney, Agent, or Firm—James H. Beusse; Douglas E. Stoner

[57] ABSTRACT

A control system for providing power to independently driven wheels of a power driven cart for transporting medical diagnostic equipment. A manually engageable handle is mounted to the cart in a position allowing a person to exert a manual force on the handle in a direction in which it is desired for the cart to move. Force sensors are coupled to the handle to sense the manual force applied to it in a plane parallel to the plane on which the cart is to be moved. The force sensors provide signals representative of the magnitude and direction of the manual force applied to the handle in forward, reverse and turning directions. Electronic circuits are coupled to the force sensors for providing control signals to motors driving the wheels of the cart for independently controlling direction and velocity of movement of the cart.

9 Claims, 10 Drawing Figures

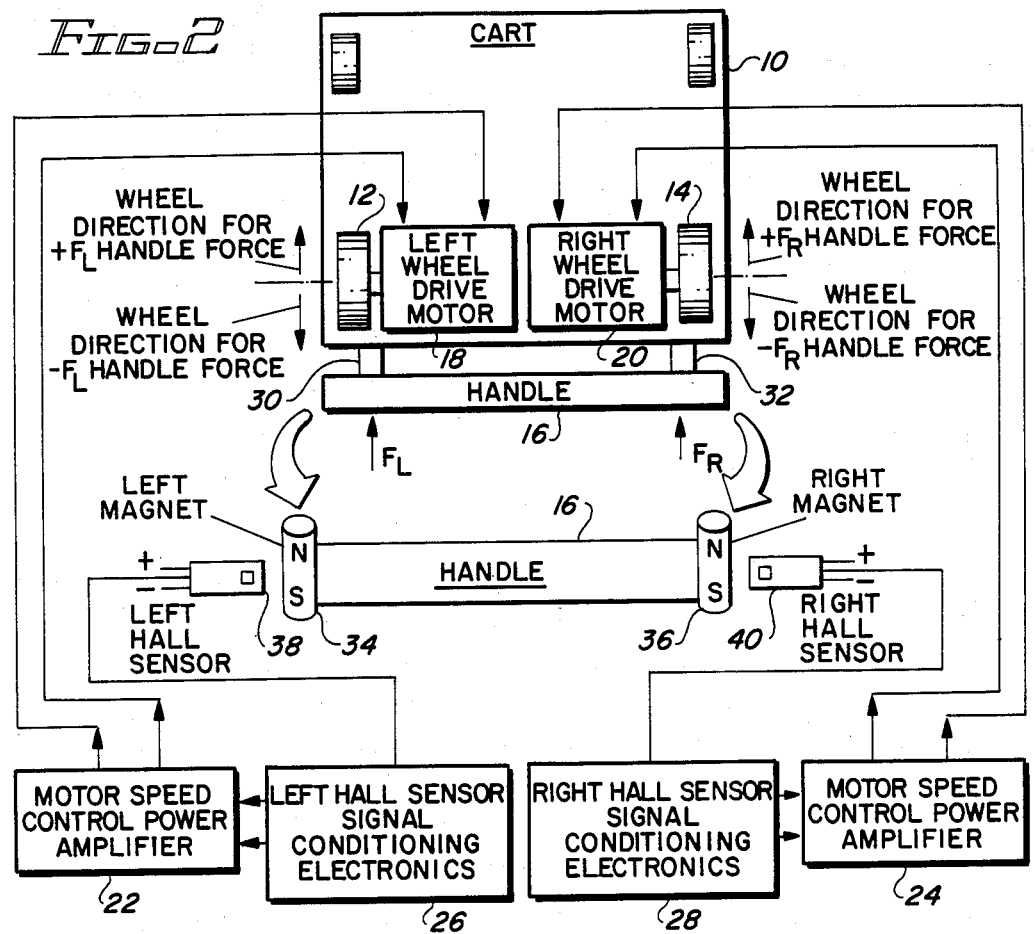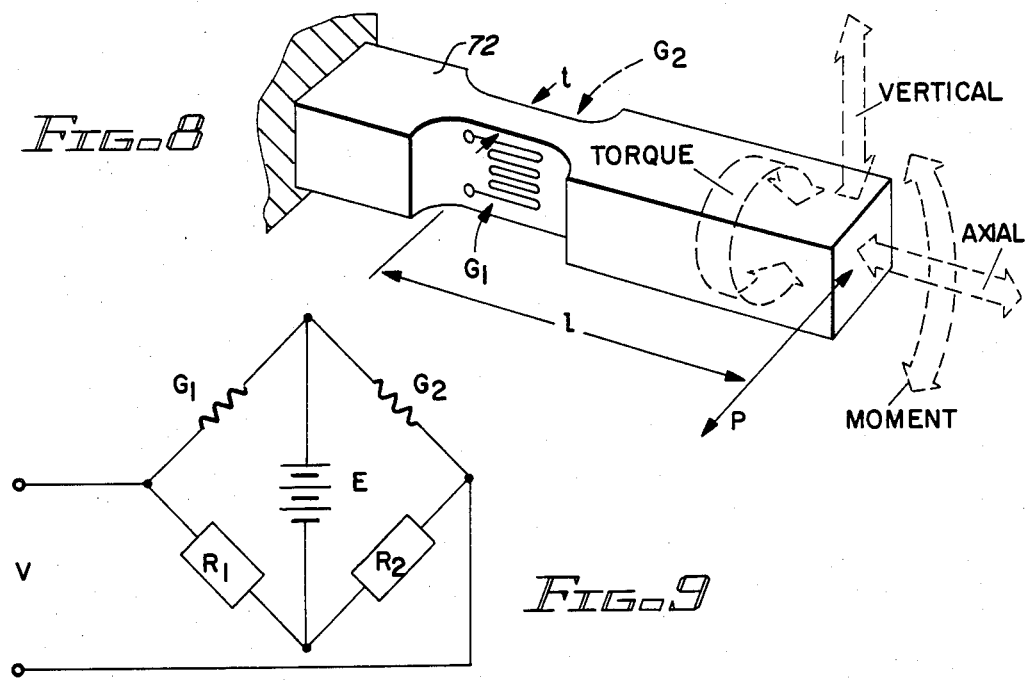

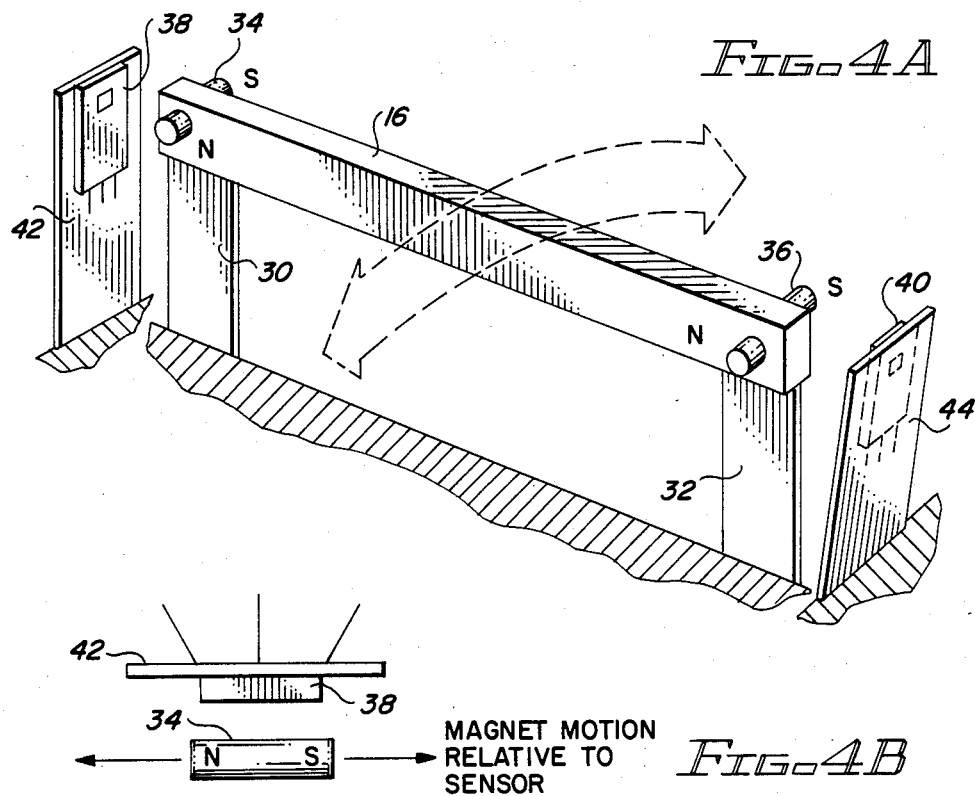
FIG. 4A
FIG. 4B
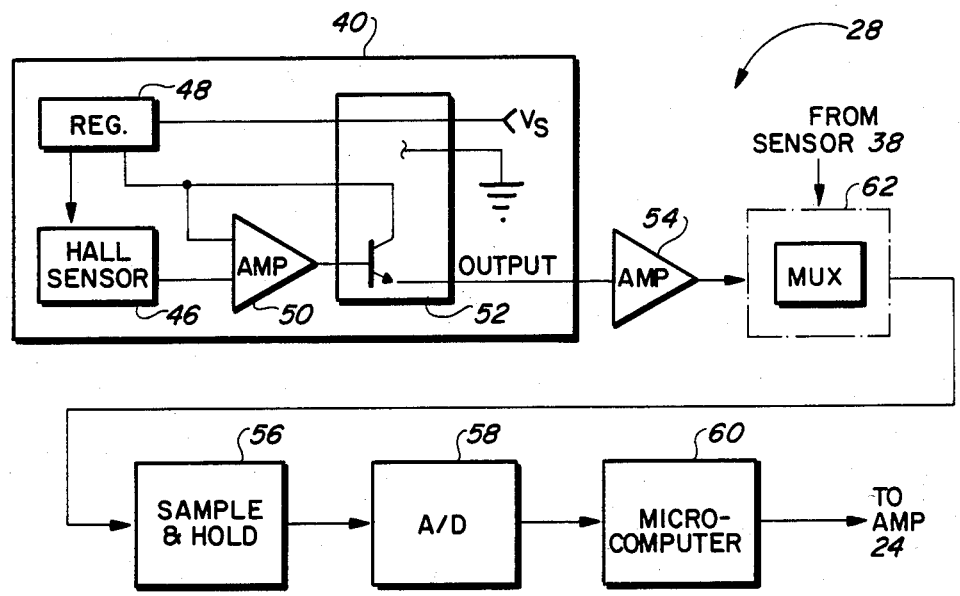
FIG. 5

DRIVE DESIGN FOR MOBILE X-RAY UNITS WITH DUAL WHEEL DRIVES

BACKGROUND OF THE INVENTION

This application relates to a power assisted cart for mobile medical diagnostic equipment and, more particularly, to a force responsive handle assembly and control system for sensing direction and magnitude of force applied to the handle and controlling motion of the cart accordingly.

It is common in medical facilities to have portable diagnostic equipment for patients who are unable to be moved. One typical type of portable equipment is a medical x-ray machine. These machines are mounted on power assisted carts, i.e., carts which are motor driven. Control of such carts is generally by an operator who stands to the rear of the cart and controls the direction of motion of the cart by positioning a switch for either forward or reverse movement. The velocity of motion is controlled by a separate lever which is operated while steering the cart. Turning the cart is not power assisted and thus requires tremendous effort since such carts may weigh as much as 1,000 pounds. Additionally, moving the cart requires an inordinate amount of skill and practice to coordinate manual steering efforts with forward/reverse switching action and simultaneous speed control.

A disadvantage of such prior cart systems is that an operator's reaction to correct the direction of travel of the powered cart is to apply additional force to the cart handle to effect a correction. However, the correction can only be effectively done by changing the position of the lever or switch type controls on the cart. Thus, it would be desireable to have a control arrangement such that the massive, heavy medical equipment cart would respond to a force on the handle in the same manner as, for example, a shopping cart.

A more specific disadvantage of prior art medical equipment carts is the relative difficulty of quickly stopping such carts in an emergency situation, such as, for example, if an operator were to inadvertently be trapped between the cart and an immoveable object. The tendency in such situations is to resist the encroaching cart by pushing on the handle. Accordingly, it would be desireable to provide a cart control arrangement responsive to force on the handle to both stop and reverse direction of a cart.

It is an object of the present invention to provide a mobile power assisted equipment cart which is easily moved and stopped by manual effort.

It is another object of the present invention to provide a mobile power assisted equipment cart which is easily steered and turned by manual effort on a handle.

SUMMARY OF THE INVENTION

This invention is directed to a mobile power assisted equipment cart such as that used for transporting and positioning medical diagnostic equipment and is particularly directed to a handle arrangement which translates force applied to the handle into control signals for driving and steering the cart. Medical equipment carts generally have fixed, non-steerable drive wheels positioned rearwardly and caster wheels positioned forwardly. The rear wheels are independently driven by electric motors. The present invention provides a horizontal handle attached to the rear of the cart in a position for normal manual engagement by an operator. At each end of the handle there is located force responsive apparatus for sensing the magnitude and direction of force applied to the handle. This force is translated into electrical signals which are applied to independent control systems for the electric drive motors.

In a preferred embodiment, the handle is supported at each end by springs cantilevered vertically from the cart. The springs are rigidly connected to the ends of the handle whereby a force exerted on the handle will result in deflection of the springs and movement of the handle. A magnet or gauss source is attached to each end of the handle and moves when the handle is moved. A Hall effect sensor is attached rigidly to the cart, adjacent to each magnet. When no force is applied to the handle the Hall sensor detects a nominal gauss level and outputs a null voltage. When a force is applied resulting in movement of the handle and magnet the voltage output changes linearly. By using a bi-polar magnet in a slide by condition, motion of the handle and thus force on the handle can be detected in two directions. The output voltage of the sensor is connected in an electrical circuit which tailors the output, making it a usable signal having both a magnitude and a polarity representative of the input force. The electric signal is coupled to a control system for regulating power to the drive motors in a manner to cause the cart to be propelled, turned or stopped in compliance with low level forces on the handle.

DESCRIPTION OF THE DRAWING

For a better understanding of the present invention, reference may be had to the following detailed description taken in conjunction with the accompanying drawings in which:

FIG. 2 is a simplified functional block diagram of a control arrangement for a mobile medical equipment cart utilizing the teaching of the present invention;

FIGS. 4A and 4B are functional illustrations of a first embodiment of a force responsive handle according to the present invention;

FIG. 5 is an exemplary circuit diagram in block form on a signal conditioning circuit for use with a Hall effect force sensor;

FIG. 8 is an exemplary illustration of one form of strain responsive arm utilized in conjunction with the handle of the present invention; and FIG. 9 is a simplified schematic of a bridge circuit of the type shown in FIG. 6.

DETAILED DESCRIPTION

Figure 1:
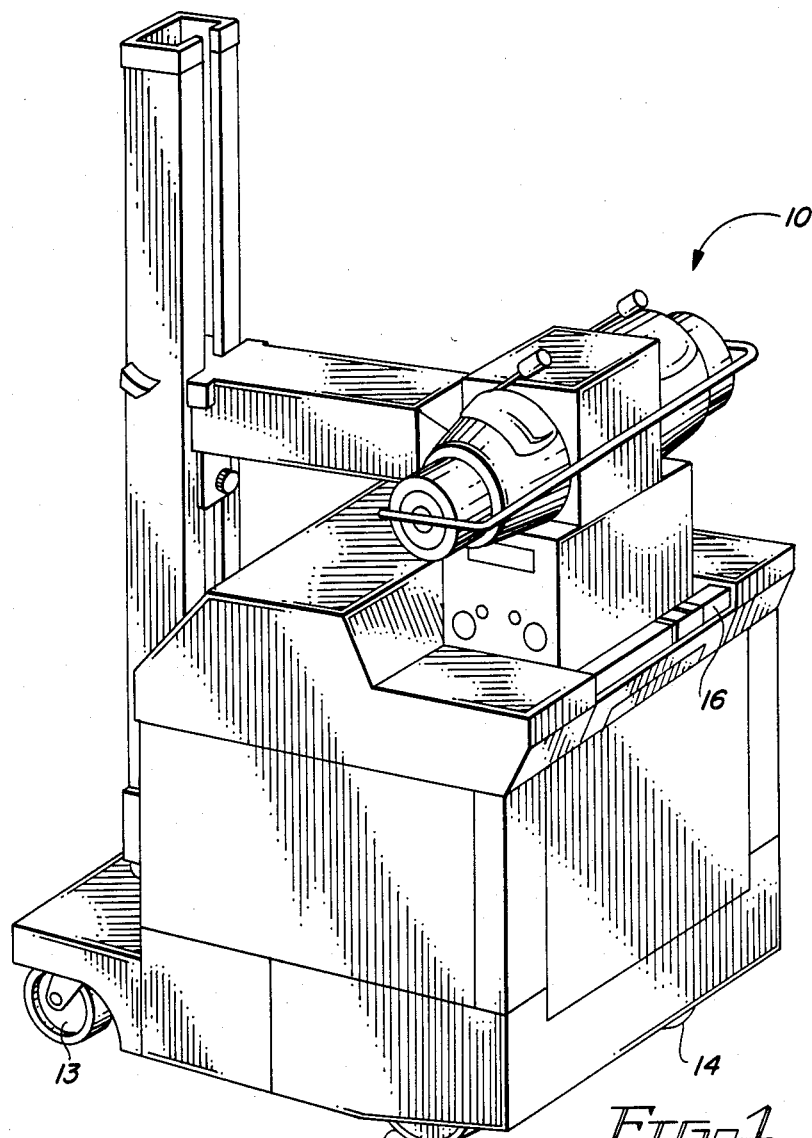
FIG. 1 is a simplified perspective view of a medical equipment cart with which the present invention is particularly useful.

Referring now to FIG. 1, there is shown a simplified illustration of a mobile medical equipment diagnostic cart 10 of the type with which the present invention is particularly useful. The diagnostic cart 10 may be, for example, a cart for transporting mobile x-ray equipment. Such carts may weigh in excess of 1,000 pounds and are thus very difficult to move without power assistance. Generally the cart 10 is provided with a pair of fixed, non-steerable wheels 12 and 14 rearwardly of the vehicle. The front of the vehicle is supported by a pair of caster wheels, one of which is shown at 13. The fixed rear wheels are generally electrically driven and powered from a dynamoelectric means such as a direct cirrent electric motor mounted in the cart. The electric motors are supplied with power from on board batteries (not shown) which increase the weight of the cart 10.

Also positioned at the rear of the cart is a handle 16 which is manually engageable by an operator to push and steer the mobile cart. In the prior art apparatus, there would also be included a switch for controlling the direction of motion of the cart, i.e., either in forward or in reverse, and a lever for controlling the speed at which the cart is driven. The prior art carts are not provided with a steering mechanism and accordingly, since both of the rear driving wheels 12 and 14 are normally driven at the same velocity, it becomes very difficult for an operator to steer or turn the cart.

Turning now to FIG. 2, there is shown a simplified functional block diagram of a system according to the present invention which incorporates propulsion and steering control into the handle 16. The cart is shown in a top view with the drive wheels 12 and 14 connected to be driven by respective drive motors 18 and 20 having rotors connected through gearing arrangements (not shown) to the wheels 12 and 14. The drive motors 18 and 20 are individually controlled by corresponding motor speed power control units 22 and 24. The motor speed power control units 22 and 24 may be of the amplifier type such as, for example, that shown in U.S. Pat. No. 4,163,929 issued Aug. 7, 1979 and assigned to General Electric Company. Other forms of power control units such as chopper circuits of a type commonly used in electrically powered vehicles might also be substituted. An example of such a chopper circuit for a direct current motor is illustrated in U.S. Pat. No. 3,843,912 issued Oct. 22, 1974 and assigned to General Electric Company. As will be appreciated, the drive motors 18 and 20 are preferably direct current motors but other types of motors could be utilized and in such cases the power units 22 and 24 might be replaced by other types of power amplifiers. An example of such an interchange would be to use electronically commutated motors in conjunction with a control system such as that shown in U.S. Pat. No. 4,449,079 issued May 15, 1984 and assigned to General Electric Company.

The power amplifiers 22 and 24 are provided with control signals from corresponding left and right force sensor signal conditioning electronic circuits 26 and 28. These two electronic circuits may also be of a type well known in the art for conditioning the signals from the corresponding force sensors into a form suitable for application to the power amplifiers 22 and 24. In general, such conditioning electronic circuits may be simple analog amplifier circuits. However, in some applications, the analog signals derived from the strain gauges may be converted to digital signals for controlling a digital power system and in such event, the conditioning electronic circuits 26 and 28 may include analog to digital converters of a type well known in the art.

In the embodiment illustrated in FIG. 2, the handle 16 is connected to the cart 10 through first and second relatively stiff but flexible members 30 and 32. The members 30 and 32 may be considered as stiff leaf springs. The spring members 30 and 32 allow the handle to be displaced slightly in both forward and reverse directions in response to corresponding forces exerted against the handle, as by pushing or pulling on it. At each end of the handle 16 there is attached one of a pair of linear magnets 34 and 36 which moves with the handle. Attached to the cart 10 and positioned adjacent each magnet 34 and 36 is a corresponding one of a pair of Hall effect sensors 38 and 40, respectively. The Hall effect sensors 38 and 40 are appropriately connected to a power source (not shown).

Figure 3:
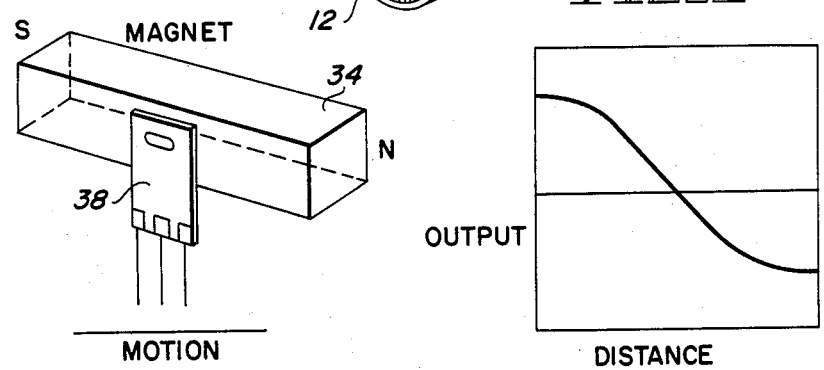
FIG. 3 illustrates Hall effect sensor output characteristics in response to relative displacement between a magnet and a sensor.
Figure 6:
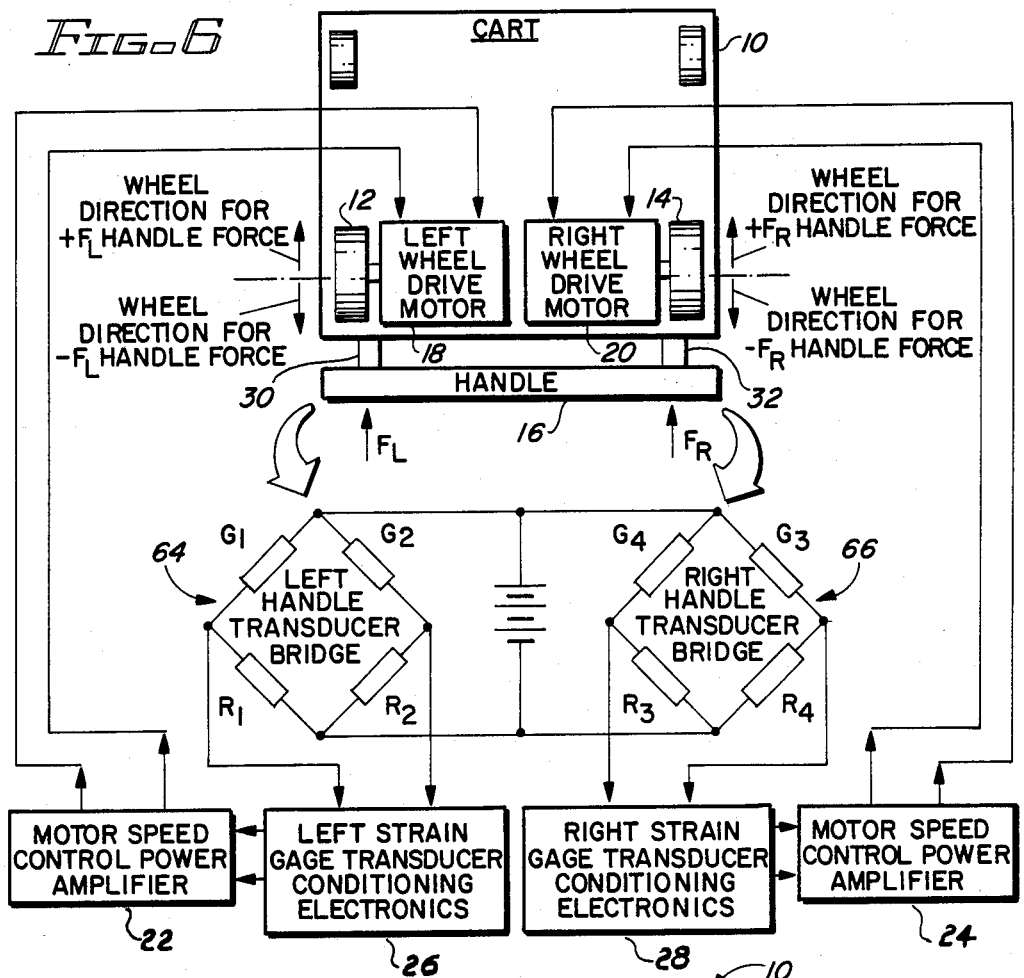
FIG. 6 is a simplified functional block diagram of an alternate form of the present invention utilizing strain responsive means for force sensors.
Figure 7:
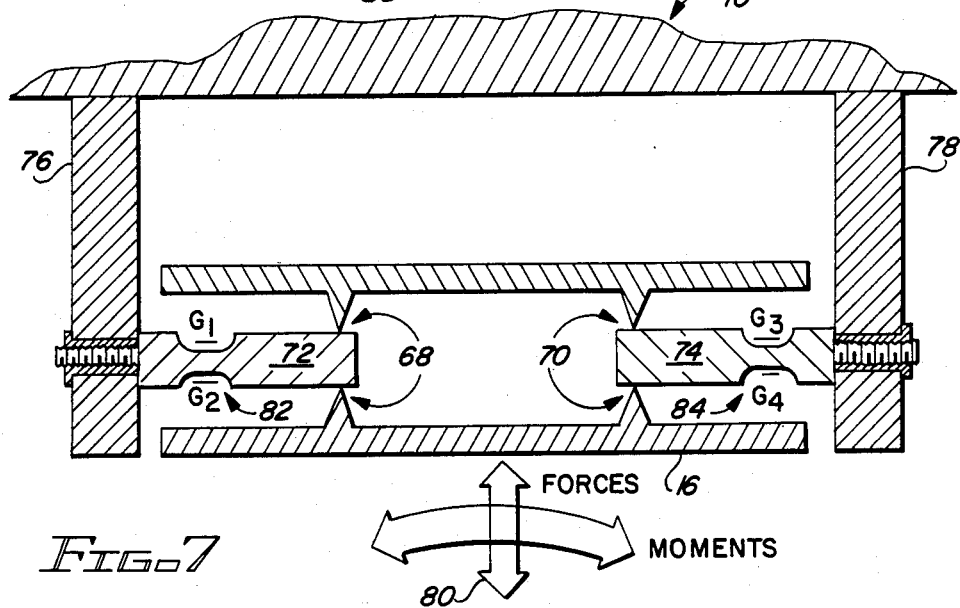
FIG. 7 is an illustration of an exemplary embodiment of a force responsive handle according to the present invention.

The sensors 38 and 40 are well known, commercially available sensors and are not described herein. Turning, however, to FIG. 3 there is shown a graph of the electrical response of one of the sensors 38 and 40 as its relative position changes with respect to an adjacently positioned one of the magnets 34 and 36. For reference, the magnet 34 is shown with respect to sensor 38 in FIG. 3. As can be seen, when the sensor 38 is centered with respect to magnet 34, the output signal from sensor 38 is at a zero level. As the magnet 34 is displaced, the sensor output signal varies approximately linearly between its maximum positive and negative values. The sign or polarity of the sensor signal is indicative of the direction in which the handle 16 is displaced while the magnitude of the signal is proportional to the amount of displacement. More particularly, the greater the force applied against the handle 16, the greater the amplitude of the sensor output signals since a greater force will result in a larger displacement of handle 16.

The mechanical arrangement or structure of the handle 16 with the Hall effect sensors is shown in more detail in FIG. 4A. In order to respond to forces exerted substantially parallel to a plane on which the cart is operated, the handle 16 is arranged to pivot about a horizontal axis by virtue of the attachment of one end of spring members 30 and 32 to the cart 10 such that the spring members extend vertically from the cart 10. The distal ends of the members 30 and 32, with respect to cart 10, are attached to opposite ends of handle 16. The spring action of members 30 and 32 allow relatively easy displacement of handle 16 while effecting a rapid return to a neutral or center position when the handle is released. The sensors 38 and 40 are attached to corresponding supports 42 and 44 which maintain a fixed position of the sensors with respect to the cart 10. The mechanical connection of any of the above elements to the cart 10 may be by any of several well known attachment means including, for example, welding, bolting or glueing. FIG. 4B is a top view of one end of handle 16 further illustrating magnet motion with respect to a one of the sensors.

Turning now to FIG. 5, there is shown one form of the signal conditioning electronic circuit 28 in a simplified block diagram format. The sensor 40 is a commercially available sensor which includes a Hall device 46, a current regulator 48, an amplifier 50 and a current driver 52. The Hall device impedance is effected by a changing magnetic field to provide a changing current which is amplified by amplifier 50 and coupled through driver 52 as the sensor output signal to the conditioning circuit 28. The circuit 28 converts the sensor output to a form for controlling the motor speed amplifier 24. As buffer amplifier 54 provides signal level translation converting the relatively low voltage output of the sensor 40 to a useable higher voltage. The voltage from amplifier 54 is supplied to a sample and hold circuit 56 of a type well known in the art. Circuit 56 allows discrete, periodic values to be sampled which are then converted to digital values by analog-to-digital converter 58 (A/D). The digital values from A/D 58 representing the sensor output are coupled to a microcomputer 60 where they are converted to appropriate drive signals for the motor speed amplifier 24.

In a preferred form, the signal conditioning electronic circuits 26 and 28 are combined into a single common circuit by use of a multiplexor (MUX) 62. As shown in FIG. 5, the MUX 62 selects one of the signals from either sensor 38 or 40 and that signal is then processed through the computer 60 and supplied to the approximate amplifier 22 or 24. The MUX 62 operates in a manner well in the art, preferably in response to timing signals from computer 60, to alternately sample sensors 38 and 40. This arrangement reduces the system cost by eliminating repetitious hardware such as dual computers 60.

Each end of the handle 16 is connected to the cart 10 through an attachment means which incorporates a strain responsive means. Typically, such strain responsive means will include a strain gauge of a type well known in the art. The strain responsive means in the illustrative embodiment comprises a pair of strain gauges at each end of the handle 16. The strain gauges are electrically connected to a pair of Wheatstone bridge circuits 30 and 32 which enables generation of signals from the strain gauges proportional to and representative of the magnitude and direction force being applied to the handle 16. The signals generated by the Wheatstone bridge circuits 30 and 32 are coupled to the respective ones of the signal conditioning electronics circuits 26 and 28. One type of signal conditioning circuit associated with a strain gage is shown and described in U.S. Pat. No. 4,107,590 issued Aug. 15, 1978 and assigned to General Electric Company. This latter patent also includes a description of a circuit for controlling a motor from a strain gage signal.

Before describing in detail the operation of the circuits 30 and 32, reference is first made to FIG. 3 in which there is shown a cross-sectional view of an exemplary embodiment of the handle 16. Shown in cross-section, the handle 16 is illustrated as a hollow handle having pivot joints 34 and 36 at each end. The pivot joints connect the handle to first and second cantilevered strain gauge transducer sensor arms 38 and 40. The arms 38 and 40 are each fixedly attached at one end to support arm structures 42 and 44, respectively. It should be noted that the view shown in FIG. 1 is a top view looking down on the handle. The normal direction of travel of the cart on which the handle 16 is mounted is in the direction of the arrow 46.

Each of the arms 38 and 40 has a necked-down or reduced cross-sectional area 48 and 50. The necked-down area serve to concentrate any bending moment applied to the arms 38 and 40 at that area. Strain gauges G1 and G2 are attached to each side of the necked-down area 48 while strain gauges G3 and G4 are attached to opposite sides of the necked-down area 50. The positioning of the strain gauges is such that detection of a bending moment exerted in a normal direction of travel of the cart 10 occurs. Any motion or torque applied to the arms 38 and 40 in a direction other than in accordance with the arrow 46 causes equal strain on each of the opposing strain gauges and therefore does not result in any differential signal. Accordingly, the handle 16 is arranged to only detect forces applied in the direction of motion of the cart 10. However, it should be noted that if one side of the handle is pushed in a forward direction while a force is exerted on the other end of the handle in a rearward direction, the arms 38 and 40 will have a bending moment in opposite directions and can therefore provide signals which will enable different polarity signals to be applied to the control electronics for the electric motors. Such an arrangement will permit the electric motors to be driven in opposite directions and allow the cart 10 to be pivoted or turned in a very small radius. Thus, the handle is sensitive to differential forces applied accross the length of the handle.

While the pivotal joints 34 and 36 have been shown as fulcrum connections between the handle 16 and the arms 38 and 40, it will be appreciated that a more practical approach is to pivotably attach the arms 38 and 40 to the handle 16 by means of pins passing through the handle and points adjacent the ends of the arms 38 and 40. The only requirement is that the ends of the arms 38 and 40 be pivotally attached to the handle 16 to allow some slight differential motion between the opposite ends of the handle.

Considering now FIG. 4, there is shown an enlarged view of one form of the arms 38 and 40 more clearly showing the placement of the strain gauges in the necked-down area of the sensor arm. As is well know, commercially available strain gauges such as those available from Kulite Semiconductor Products, Inc. are in the form of patterned serpentine resistive networks which can be affixed to a surface. Any stress or strain applied to that surface will cause either a elongation or contraction of the strain gauge. As was indicated in FIG. 2, there are two strain gauges associated with each of the sensor arms and both of these strain gauges are connected in a Wheatstone bridge electrical circuit. In consequence, the bridge circuit permits discrimmination between signals indicative of differential changes in the gauges G1 and G2 or G3 and G4 as opposed to common changes in each gauge. In FIG. 4, the motion of the arm in the direction of the arrow 52 will result in contraction of one of the gauges and elongation of the other. This motion will result in a differential change of the resistance of the gauges. Any motion of the arm 38 along any of the dashed lines 54, 56, 58 and 60 will result in equal contraction or elongation of the strain gauges G1 and G2 and thus preclude any differential change in their resistance.

Considering now FIG. 5, the two strain gauges, G1 and G2 are shown connected in a Wheatstone bridge circuit of the type shown in FIG. 2. The two resistors R1 and R2 completing the bridge circuits are fixed resistors and selected to have values to balance the bridge circuit. Selection of such resistors is well known in the art and will not be described herein. The voltage output of the Wheatstone bridge circuit can be expressed by the equation:

$$V = (SEK)/2$$

Where S represents the strain, E is excitation voltage and K is a strain gauge constant. The value of strain S is determined by the well known equation $12PL/BT^2$ for a cantilevered arm. In the strain gauge equation, P represents the load applied to the cantilevered end of the arm, L is the length of the arm, B is the width of the arm in a direction perpendicular to the applied force and T is the thickness of the arm at the point at which bending occurs. By substituting the strain gauge equation into the equation for the output voltage V of the Wheatstone bridge circuit, it can be seen that the voltage V is equal to $6PLEK/BT_2$. Thus, the voltage output of the Wheatstone bridge circuit of FIG. 5 is directly proportional to the amount of strain force applied to the handle 16. Furthermore, the polarity of the voltage V is indicative of the direction in which the associated sensor arm 38 or 40 is being bent. The signal voltage V can therefore be used to control the velocity and direction of rotation of the wheels 12 and 14.

There has been described a system for controlling independently drive motors of a mobile medical equipment cart so as to make the cart easily propelled and steered. While the invention has been described with reference to a specific embodiment, it is realized that modifications and changes will occur to those skilled in the art. It is, therefore, to be understood that the appended claims are intended to cover all such modifications and changes as fall within the true spirit and scope of the invention.

We claim:

1. A control system for providing power to at least one pair of independently driven wheels of a power driven cart for transporting medical diagnostic equipment, the control system comprising:

a manually engageable handle having first and second ends and being mounted to the cart in a position allowing a manual force to be exerted on the handle substantially in a direction in which movement of the cart is desired;

force responsive means coupled to said handle for sensing the manual force applied to said handle in a horizontal plane substantially parallel to said direction of movement, said force responsive means providing signals representative of the magnitude and direction of the manual force applied to each of said first and second ends of said handle;

means responsive to the signals for actuating the control system to provide the power to the driven wheels independently for controlling the direction and velocity of movement of the cart; and said handle comprising a bar having pivotable mounts at each of said first and second ends, said force responsive means including first and second cantilevered arms each having one end fixedly mounted to the cart adjacent a corresponding one of said first and second ends of said handle, a second end of each of said arms being coupled to a corresponding one of said pivotable mounts, the manual force applied to said handle causing a bending of said arms, said force responsive means further including means responsive to the magnitude and direction of bending for producing said magnitude and direction signals.

2. The control system of claim 1 wherein said arms each have a predefined bending area and including:

a pair of strain responsive electrical resistance means attached to opposite sides of said bending area, said resistance means having the property of varying its electrical resistance in response to bending at said bending area; and electrical circuit means responsive to variations in said resistance means for providing the signals.

3. The control system of claim 2 wherein said circuit means comprises a Wheatstone bridge having said resistance means connected to form two legs of said bridge.

4. The control system of claim 1 wherein said force responsive means comprises magnet means attached to each of said first and second ends of said handle, said Hall effect sensors being positioned adjacent said magnet means and attached to said cart.

5. The control system of claim 4 wherein said handle is attached to said cart by vertically extending relatively stiff spring members, said spring members deflecting horizontally to allow displacement of said handle in proportion to the applied force.

6. A control system for providing power to at least one pair of independently driven wheels of a power driven cart for transporting medical diagnostic equipment, the control system comprising:

a manually engageable handle having first and second ends and being mounted to the cart in a position allowing a manual force to be exerted on the handle substantially in a direction in which movement of the cart is desired;

force responsive means coupled to said handle in a horizontal plane substantially parallel to said direction of movement, said force responsive means providing signals representative of the magnitude and direction of the manual force applied to each of said first and second ends of said handle;

means responsive to the signals for actuating the control system to provide the power to the driven wheels independently for controlling the direction and velocity of movement of the cart, said force responsive means comprising at least one Hall effect sensor coupled to one of said handle and said cart and a magnetic means coupled to the other of said handle and said cart, said sensor being arranged to provide said force responsive signals in responsive to relative displacement of said handle.

7. An electrically powered medical diagnostic equipment cart comprising:

at least first and second wheels positioned on opposite sides of the cart;

first and second electric drive motors coupled in driving relationship to respective ones of said at least first and second wheels;

first and second motor speed control circuits connected to supply electrical power to said first and second motors so as to drive them in both a forward and reverse direction, respectively;

a manually engageable handle coupled to the cart through first and second strain responsive means at opposing ends of said handle, said strain responsive means providing indications of the direction and degree of force at each end of said handle in response to a manually applied force;

first and second means each responsive to the indications from said strain responsive means for generating magnitude and direction signals to respective ones of said speed control circuits for effecting motion of the cart in accordance with force on said handle, respectively, said handle comprising a finite length bar having magnet means attached to opposite ends thereof, said force responsive means including Hall effect sensore mounted to said cart adjacent said magnet means, deflection of said handle causing relative displacement between said magnet means and an adjacent one of said sensors, said sensors being responsive to displacement of said magnet means for providing said indications of said direction and degree of force applied to said handle.

8. The equipment cart of claim 7 wherein said handle is attached to said cart by vertically extending relatively stiff spring members, said spring members deflecting horizontally to allow displacement of said handle in proportion to the applied force.

9. A control system for providing power to at least one pair of independently driven wheels of a power driven cart for transporting medical diagnostic equipment, the control system comprising:

a manually engageable handle having first and second ends and being mounted to the cart in a position allowing a manual force to be exerted on the handle substantially in a direction in which movement of the cart is desired;

force responsive means coupled to said handle for sensing the manual force applied to said handle in a horizontal plane substantially parallel to said direction of movement, said force responsive means providing signals representative of the magnitude and direction of the manual force applied to each of said first and second ends of said handle;

means responsive to the signals for actuating the control system to provide the power to the driven wheels independently for controlling the direction and velocity of movement of the cart; and said handle including force responsive means coupled to each of said first and second ends and said force responsive means comprising a Hall effect sensor.

* * * * *